(«12) United States Patent
Nakayama

(10) Patent No.: US 9,214,139 B2
(45) Date of Patent: Dec. 15, 2015

(54) IMAGE DISPLAY APPARATUS AND IMAGE DISPLAY METHOD

(75) Inventor: Michito Nakayama, Utsunomiya (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 308 days.

(21) Appl. No.: 12/553,277

(22) Filed: Sep. 3, 2009

(65) Prior Publication Data

US 2010/0085273 A1 Apr. 8, 2010

(30) Foreign Application Priority Data

Oct. 2, 2008 (JP) ................................. 2008-257680

(51) Int. Cl.
G09G 5/00 (2006.01)
G09G 5/397 (2006.01)
A61B 1/00 (2006.01)
G06T 19/00 (2011.01)
A61B 1/04 (2006.01)

(52) U.S. Cl.
CPC .............. *G09G 5/397* (2013.01); *A61B 1/0005* (2013.01); *G06T 19/003* (2013.01); *A61B 1/042* (2013.01); *G06T 2210/41* (2013.01); *G06T 2219/028* (2013.01); *G09G 2380/08* (2013.01)

(58) Field of Classification Search
None
See application file for complete search history.

(56) References Cited

U.S. PATENT DOCUMENTS

| 7,149,564 | B2 * | 12/2006 | Vining et al. .................. 600/425 |
| 7,349,563 | B2 * | 3/2008 | Kiraly et al. ................... 382/128 |
| 7,640,050 | B2 * | 12/2009 | Glenn et al. .................... 382/128 |
| 2009/0309874 | A1 * | 12/2009 | Salganicoff et al. ........... 345/419 |

FOREIGN PATENT DOCUMENTS

| JP | 2007-195685 | 8/2007 |
| WO | WO 2005/011501 | 2/2005 |
| WO | WO 2007/129493 | 11/2007 |

OTHER PUBLICATIONS

Japanese Office Action issued Dec. 11, 2012 in Japanese Patent Application No. 2008-257680 filed Oct. 2, 2008.

* cited by examiner

*Primary Examiner* — Joseph Haley
(74) *Attorney, Agent, or Firm* — Oblon, McClelland, Maier & Neustadt, L.L.P.

(57) ABSTRACT

An image display apparatus has: a first image generator that defines each position between a predetermined start point and end point of a tubular structure as a first viewpoint and generates a first image obtained by observing an image of the inside of the tubular structure from each first viewpoint toward the end point; a second image generator that defines each position between the start point and the end point as a second viewpoint and generates a second image obtained by observing an image of the inside of the tubular structure from each second viewpoint toward the start point; and a user interface that is provided with an operation part, a monitor and a display controller and is configured so that, in response to an instruction from the operation part, the display controller makes the monitor display the first image and the second image.

9 Claims, 7 Drawing Sheets

FIG. 4

| OBSERVATION POINT (CENTRAL POSITION) | FIRST VIEWPOINT MOVEMENT POSITION | SECOND VIEWPOINT MOVEMENT POSITION | FIRST IMAGE ADDRESS | SECOND IMAGE ADDRESS |
|---|---|---|---|---|
| $S_0$ | | $S_{+20}$ | $P1_{-20}$ | $P2_{+20}$ |
| $S_1$ | | $S_{+21}$ | $P1_{-19}$ | $P2_{+21}$ |
| * | | * | * | * |
| $S_{k+19}$ | $S_{-1}$ | $S_{k+39}$ | $P1_{k-1}$ | $P2_{k+39}$ |
| $S_{k+20}$ | $S_k$ | $S_{k+40}$ | $P1_k$ | $P2_{k+40}$ |
| $S_{k+21}$ | $S_{k+1}$ | $S_{k+41}$ | $P1_{k+1}$ | $P2_{k+41}$ |
| * | * | * | * | * |
| * | * | * | * | * |
| $S_n$ | $S_{n-20}$ | $S_{n+20}$ | $P1_{n-20}$ | $P2_{n+20}$ |

IMAGE DISPLAY APPARATUS AND IMAGE DISPLAY METHOD

BACKGROUND OF THE INVENTION

1. Field of the Invention

The present invention relates to an image display apparatus and an image display method. To be specific, the present invention relates to an image display apparatus and an image display method for extracting data of a tubular structure from volume data acquired by imaging a subject including the tubular structure, generating an image of the inside of the tubular structure by surface rendering, and displaying the generated image of the inside of the tubular structure on a monitor.

2. Description of the Related Art

The abovementioned type of image display apparatus sets a viewpoint in a tubular structure at all times, moves the viewpoint in one direction from one end to the other end of the tubular structure, generates an image obtained by observing the inside of the tubular structure at the viewpoint toward the destination of the movement (in the one direction) at every movement position of the viewpoint, and stores the generated image into a storage. In response to designation of the viewpoint by an operation part, the image display apparatus reads out the image of the inside of the tubular structure in the one direction corresponding to the movement position of the viewpoint from the storage, and displays the read-out image on a monitor (Japanese Unexamined Patent Application Publication No. 2007-195685).

The abovementioned technique is called a virtualized endoscope system (VES). The VES is used in various clinical sites, for example, in a test on the large intestine. The image display apparatus described in JP-A 2007-195685 is the VES, which is a technique for displaying, on a monitor, an image obtained by observing the inside of a tubular structure from a viewpoint toward the destination of movement (in one direction).

However, there is a problem in use of the abovementioned technique (VES) for a test on the large intestine. Protrusions such as haustra exist inside a tubular structure, i.e., inside the large intestine.

When the inside of the tubular structure is observed at the viewpoint toward the destination of movement (in one direction), the protrusions create blind spots, which may make it impossible to easily find a lesion site or the like.

SUMMARY OF THE INVENTION

The present invention is created in order to solve the abovementioned problem. An object of the present invention is to provide an image display apparatus and an image display method that make it possible to easily and certainly find a lesion site or the like by observing the inside of a tubular structure from both directions and thereby preventing creation of blind spots by protrusions.

A first aspect of the present invention is an image display apparatus that extracts data of a tubular structure from volume data acquired by imaging a subject including the tubular structure, moves a viewpoint so as to pass through the inside of the tubular structure, and displays an image generated by observing an image of the inside of the tubular structure at the viewpoint, the image display apparatus comprising: a first image generator configured to define respective positions between a predetermined start point and end point of the tubular structure as first viewpoints and generate a first image generated by observing an image of the inside of the tubular structure on the side of the end point from each of the first viewpoints; a second image generator configured to define respective positions between the start point and the end point as second viewpoints and generate a second image generated by observing an image of the inside of the tubular structure on the side of the start point from each of the second viewpoints; and a user interface including an operation part, a monitor, and a display controller, the display controller displaying the first image and the second image on the monitor in response to an instruction from the operation part.

According to the first aspect, since the first and second images acquired by observing the inside of the tubular structure from both the directions are displayed on the monitor, blind spots are not created by protrusions existing inside the tubular structure. Consequently, it is possible to certainly find a lesion site or the like.

Further, a second aspect of the present invention is the image display apparatus according to the first aspect, in which the display controller is configured to simultaneously display, on the monitor, the first and second images generated by observing, from both the viewpoints, a region having a predetermined width between the first and second viewpoints moving while keeping a predetermined distance from each other.

According to the second aspect, since the first and second images acquired by observing regions having the same predetermined widths in the tubular structure from both the directions are simultaneously displayed on the monitor, blind spots are not created by protrusions existing inside the tubular structure. Consequently, it is possible to certainly find a lesion site or the like.

Further, a third aspect of the present invention is the image display apparatus according to the first aspect, further comprising a movement line determining part configured to determine a movement line passing through the inside of the tubular structure, in which: the first image generator is configured to generate the first image generated by observing the image of the inside of the tubular structure at the first viewpoint moved along the movement line; the second image generator is configured to generate the second image generated by observing the image of the inside of the tubular structure at the second viewpoint moved along the movement line; and the display controller is configured to, in response to designation of a point on the movement line by the operation part, simultaneously display, on the monitor, the first image corresponding to the designated point and the second image corresponding to the designated point.

Further, a fourth aspect of the present invention is the image display apparatus according to the first aspect, further comprising a movement line determining part configured to determine a movement line passing through the inside of the tubular structure, in which: the first image generator is configured to generate the first image obtained by moving the first viewpoint along the movement line; the second image generator is configured to generate the second image obtained by moving the second viewpoint along the movement line; and the display controller is configured to display, on the monitor, the first image corresponding to a movement position of the first viewpoint in response to designation of the movement position of the first viewpoint by the operation part, and the second image corresponding to a movement position of the second viewpoint in response to designation of the movement position of the second viewpoint by the operation part.

Further, a fifth aspect of the present invention is the image display apparatus according to the second aspect, further comprising a width changing part configured to change the predetermined width in response to designation by the operation part.

Further, a sixth aspect of the present invention is the image display apparatus according to the second embodiment, in which the display controller is configured to display each coordinate of the central position of the predetermined width on the monitor.

Further, a seventh aspect of the present invention is the image display apparatus according to the fifth aspect, in which the display controller is configured to display each coordinate of the central position of the predetermined width on the monitor.

Further, an eighth aspect of the present invention provides an image display method, comprising: extracting data representing a tubular structure based on a predetermined threshold from volume data acquired by imaging a subject including the tubular structure, and determining a movement line passing through the inside of the tubular structure; while moving a first viewpoint from a predetermined start point to a predetermined end point along the movement line, generating a first image of the inside of the tubular structure of a movement destination of the first viewpoint from the first viewpoint for every movement position of the first viewpoint; while moving a second viewpoint from the predetermined end point to the predetermined start point along the movement line, generating a second image of the inside of the tubular structure of a movement destination of the second viewpoint from the second viewpoint for every movement position of the second viewpoint; when a point on the movement line is designated by the operation part, by a display controller, simultaneously displaying the first image corresponding to the point designated by the operation part and the second image corresponding to the point designated by the operation part, on the monitor; in response to an instruction by the operation part to change a predetermined width of the inside of the tubular structure displayed on the monitor, changing the predetermined width and generating the first image based on the changed predetermined width; in response to an instruction by the operation part to change the predetermined width, changing the predetermined width and generating the second image based on the changed predetermined width; by the display controller, displaying the first image corresponding to the movement position of the first viewpoint in response to designation of the movement position of the first viewpoint by the operation part, and displaying the second image corresponding to the movement position of the second viewpoint in response to designation of the movement position of the second viewpoint by the operation part, on the monitor; and by the display controller, displaying coordinates of positions on the movement line on the monitor, the coordinates being coordinates of the central position of the predetermined width of the movement destination of the first viewpoint and coordinates of the central position of the predetermined width of the movement destination of the second viewpoint.

According to the eighth aspect, since the predetermined width is adjusted, it is possible to gradually specify the position of a lesion site or the like. Further, since the coordinates of the central position of the predetermined width are displayed, it is possible to specify the position of a lesion site or the like by displaying the lesion site or the like in the central position of the predetermined width.

BRIEF DESCRIPTION OF THE DRAWINGS

FIG. 4 is an explanatory diagram of the data structure of the first and second images and so on according to the embodiment of the present invention.

DETAILED DESCRIPTION OF THE EMBODIMENTS (Configuration)

An embodiment of an apparatus according to the present invention will be described below with reference to FIGS. 1 to 6.

Figure 1:
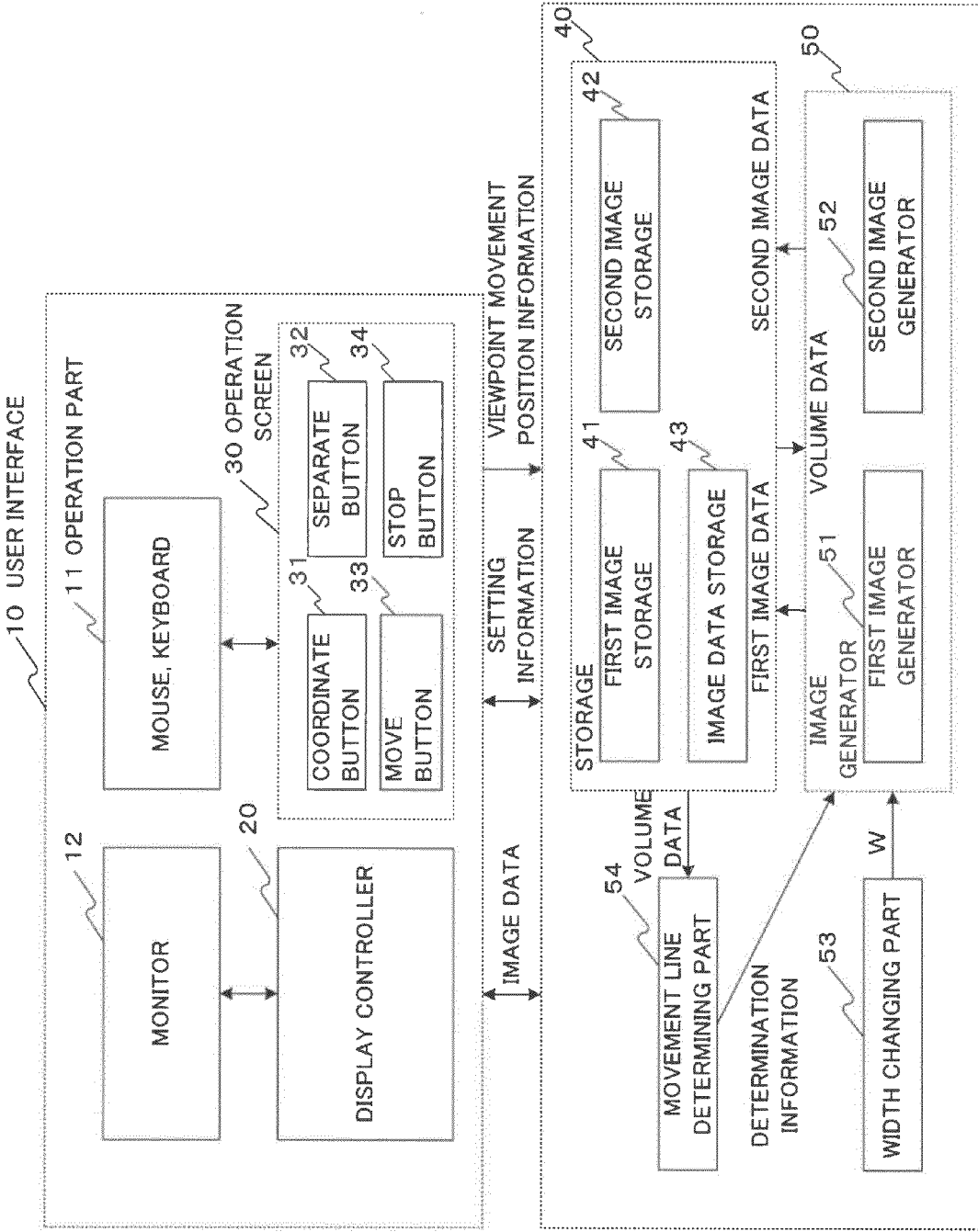
FIG. 1 is a functional block diagram of an image display apparatus according to an embodiment of the present invention.
Figure 2:
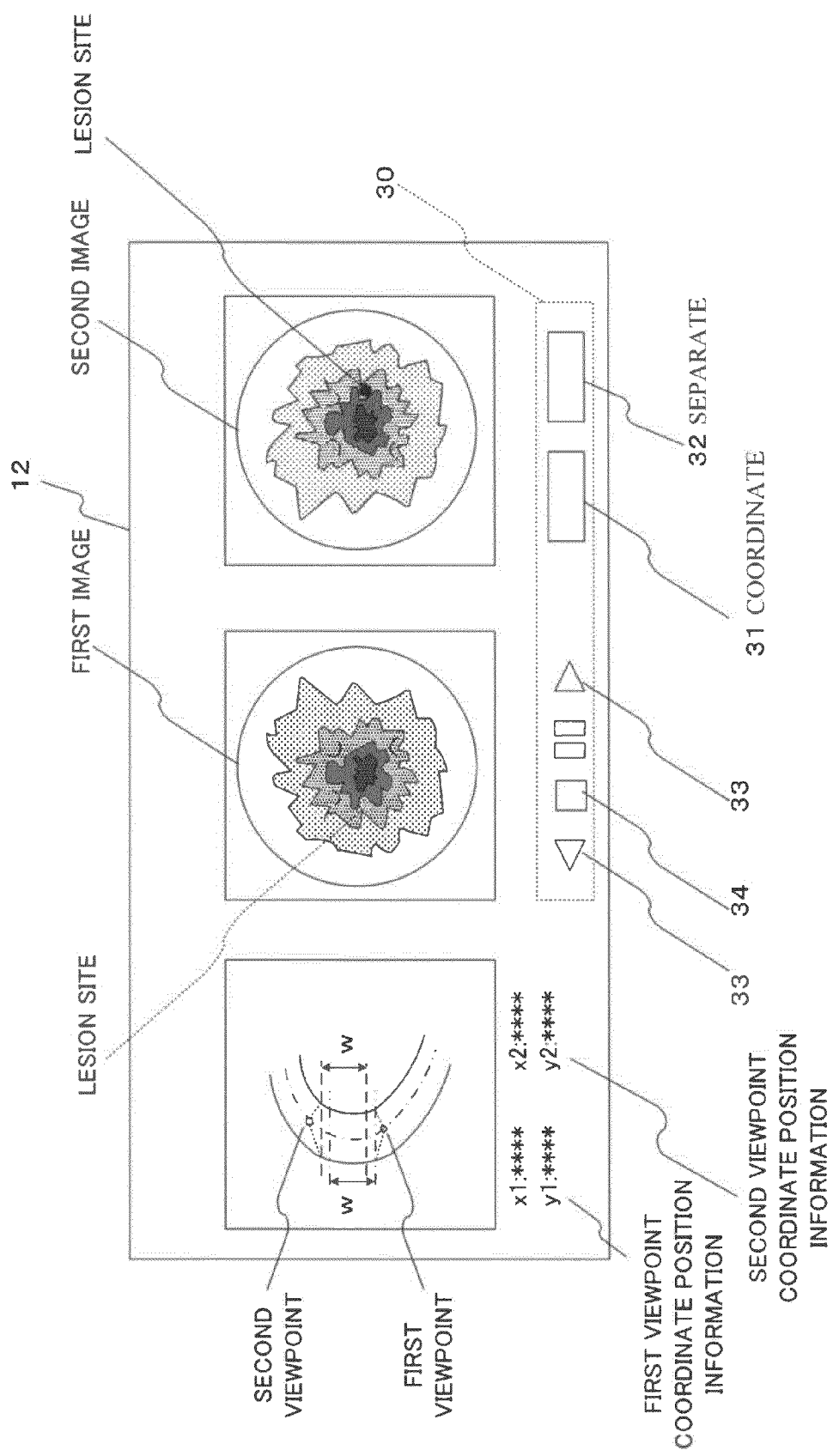
FIG. 2 is a view showing first and second images displayed on a monitor according to the embodiment of the present invention.
Figure 3:
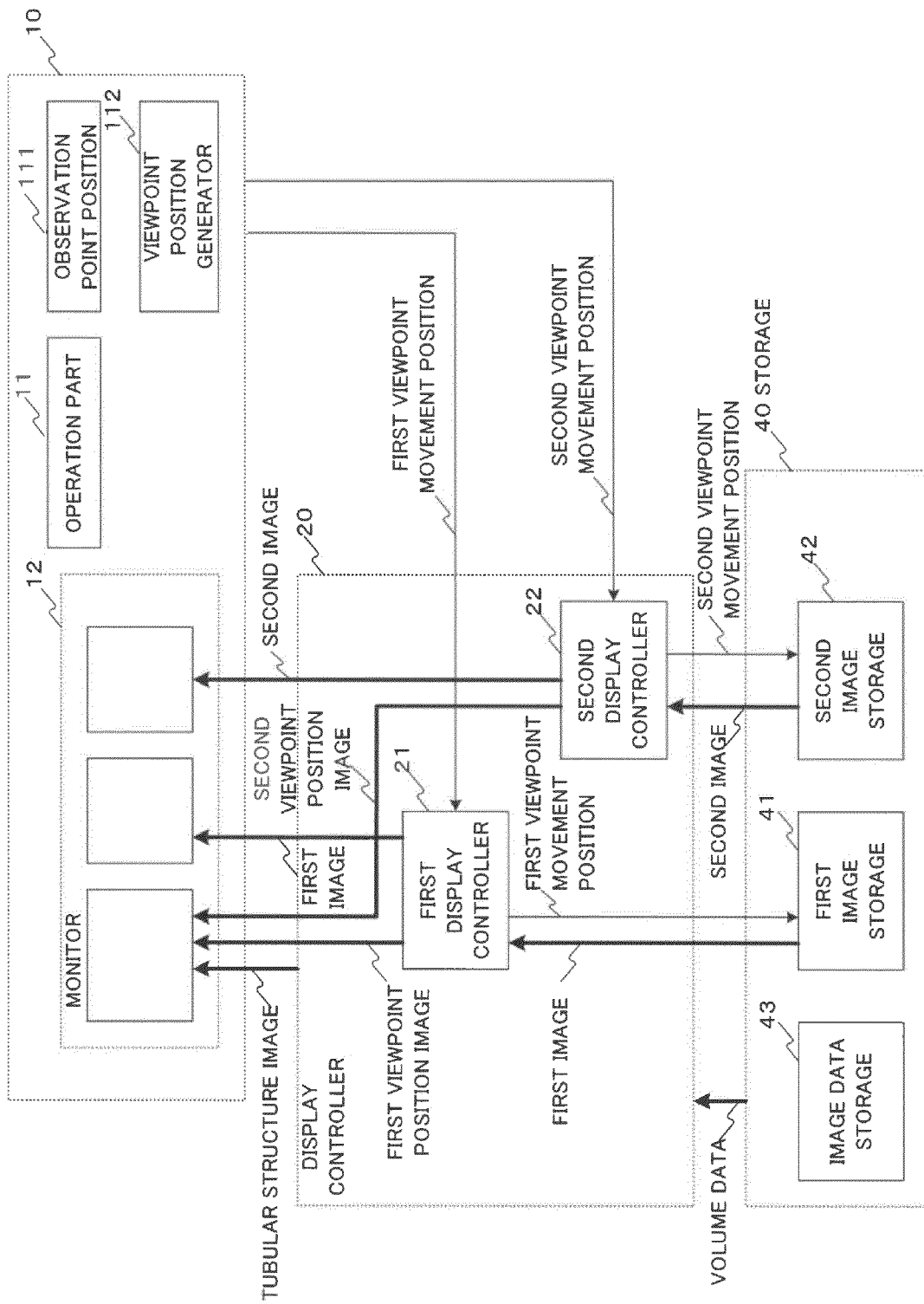
FIG. 3 is a functional block diagram of a user interface according to the embodiment of the present invention.

FIG. 1 is a functional block diagram of an image display apparatus. FIG. 2 is a view showing first and second images displayed on a monitor. FIG. 3 is a functional block diagram of a user interface.

Volume data acquired by imaging a subject including a tubular structure is stored in an image data storage 43 of a storage 40. When an image display application is executed, a menu is displayed on a monitor 12. When determination of a movement line is selected from the menu, a movement line determining part 54 extracts data representing the tubular structure based on a predetermined threshold from the volume data and determines a movement line passing through the inside of the tubular structure. A display controller 20 displays the tubular structure and the movement line on the monitor 12.

When setting of an observation object is selected from the menu, the display controller 20 displays a start point mark (not shown in the drawings) and an end point mark (not shown not shown in the drawings) on the monitor. The start point mark is moved to an arbitrary position on the movement line by an operation part 11, which is a mouse, and a start point of the observation object is designated by mouse click. In the same way, the end point mark is moved to an arbitrary position on the movement line by the operation part 11, and an end point of the observation object is designated by mouse click.

Without moving the start point mark or the end point mark by the operation part 11, one end of the movement line can be designated as the default value of the start point of the observation object and the other end of the movement line can be designated as the default value of the end point of the observation object only by mouse click. In this case, a region between the one end and the other end on the movement line is the observation object.

When the start point and the end point on the movement line are designated, an image generator 50 calculates a total length L between the start point and the end point on the movement line and divides the total length L by a predetermined pitch $\Delta S$, thereby obtaining a number n of first viewpoints on the movement line. Thus, a position $S_0$ of the start point and a position $S_n$ of the end point on the movement line are determined. The default value of the predetermined pitch $\Delta S$ is 1 (mm).

When change of the pitch is selected from the menu, in response to the designation by the operation part 11, which is a keyboard, the image generator 50 changes the predetermined pitch $\Delta S$. For example, the image generator 50 changes the predetermined pitch $\Delta S$ in a range between 0.2 mm and 5 mm.

When generation of an image is selected from the menu, while moving the first viewpoint from the predetermined start point position $S_0$ toward the predetermined end point position $S_n$ along the movement line, a first image generator 51 generates, by surface rendering, a first image obtained by observing the inside of the tubular structure from the first viewpoint at every movement position of the first viewpoint across a predetermined width W of the movement destination of the first viewpoint. Then, the first image generator 51 links the first image to the movement position of the first viewpoint and stores the image into a first image storage 41. The default value of the predetermined width W is 20 (mm). When change of the predetermined width is selected from the menu, a width changing part 53, in response to the designation by the operation part 11 that is a keyboard, changes the predetermined width W. For example, the width changing part 53 changes the predetermined width W in a range between 5 mm and 50 mm. The predetermined width W is set so as to be equal to or more than the predetermined pitch $\Delta S$ (W≥$\Delta S$).

Further, while moving the second viewpoint from the predetermined start point position $S_0$ toward the predetermined end point position $S_n$ along the movement line, a second image generator 52 generates, by surface rendering, a second image obtained by observing the inside of the tubular structure from the second viewpoint at every movement position of the second viewpoint across the predetermined width W of the movement destination of the second viewpoint. Then, the second image generator 52 links the second image to the movement position of the second viewpoint and stores the image into a second image storage 42. The movement position of the observation point is the central position between the first viewpoint and the second viewpoint, and is also the movement position of the predetermined width W.

The first image and the second image may be generated by volume rendering so that, for example, the opacity of the vascular wall is increased and the opacity of the luminal portion is decreased. In a case that it is possible to immediately generate the first image and the second image based on the movement positions of the viewpoints, it is unnecessary to link the first image to the movement position of the first viewpoint to store the image into the first image storage 41, and it is unnecessary to link the second image to the movement position of the second viewpoint to store the image into the second image storage 42.

The image generator 50 obtains the slope of the movement line at the start point position $S_0$, extends the movement line with the slope, and puts $S_{-1}$ to $S_{-20}$ on the extended movement line. The image generator 50 also obtains the slope of the movement line at the end point position $S_n$, extends the movement line with the slope, and puts $S_{n+1}$ to $S_{n+20}$ on the extended movement line.

The movement positions of the first viewpoint are denoted by $S_{-20}$ to $S_{n-20}$. The movement positions of the second viewpoint are denoted by $S_{+20}$ to $S_{n+20}$. The movement positions of the observation point are denoted by $S_0$ to $S_n$.

In this embodiment, the first image generator 51 generates the first image obtained by observing the inside of the tubular structure from the first viewpoint at every movement position of the first viewpoint (from $S_{-20}$ to $S_{n-20}$) across the predetermined width W of the movement destination of the first viewpoint. The second image generator 52 generates the second image obtained by observing the inside of the tubular structure from the second viewpoint at every movement position of the second viewpoint (from $S_{+20}$ to $S_{n+20}$) across the predetermined width W of the movement destination of the second viewpoint.

Next, the data structure of the storage 40 will be described with reference to FIG. 4. FIG. 4 is an explanatory diagram of the data structure of the storage 40.

The storage 40 stores data in arrays. The respective data arrays of the observation point movement position (central position), the first viewpoint position, the second viewpoint position, the first image address and the second image address are shown in FIG. 4. The data of the observation point movement positions (central positions) $S_0$ to $S_n$ are linked to the first viewpoint position, the second viewpoint position, the first image addresses and the second image addresses and stored in the storage 40. Instead of the address, a pointer may be employed.

Since the data are stored in arrays, it is possible to read out the first image and the second image in the following manner.

When a COORDINATE button 31 and a MOVE button 33 shown in FIG. 1 are designated by the operation part 11, an observation point position designating part 111 of the user interface 10 sequentially designates the observation point movement positions (central positions) $S_0$ to $S_n$. In response to the designation of the observation point movement positions (central positions) $S_0$ to $S_n$, the display controller 20 obtains the first image addresses $P1_{-20}$ to $P1_{n-20}$ and reads out the first image data stored in the first image storage 41 based on the first image addresses. Further, in response to the data of the observation point movement positions (central positions) $S_0$ to $S_n$, the display controller 20 obtains the second image addresses $P2_{+20}$ to $P1_{n+20}$ and reads out the second image data stored in the second image storage 42 based on the second image addresses.

The designation of the COORDINATE button 31 described above enables simultaneous display of the first image and the second image corresponding to the observation point movement positions on the monitor. The simultaneous display of the first image and the second image on the monitor will be described later.

The above description is an explanation of the first and second images read out of the storage 40 by the display controller 20 based on the observation point movement positions.

Next, the first and second images read out of the storage 40 by the display controller 20 based on the first viewpoint movement position or the second viewpoint movement position will be described.

When a SEPARATE button 32 and the MOVE button 33 shown in FIG. 1 are designated by the operation part 11 and the first viewpoint is designated by the operation part 11, a viewpoint position generator 112 of the user interface 10 sequentially designates the first viewpoint movement positions $S_{-20}$ to $S_{n-20}$. In response to the designation of the first viewpoint movement positions $S_{-20}$ to $S_{n-20}$, the display controller 20 obtains the first image addresses $P1_{-20}$ to $P1_{n-20}$ and reads out the first image data stored in the first image storage 41 based on the first image addresses.

The designation of the SEPARATE button 32 described above enables display of the first image corresponding to the first viewpoint movement position on the monitor. In this case, the second image is displayed on the monitor without being changed. The display of the first image on the monitor will be described later.

On the other hand, when the SEPARATE button 32 and the MOVE button 33 shown in FIG. 1 are designated by the operation part 11 and the second viewpoint is designated by the operation part 11, the viewpoint position generator 112 of the user interface 10 sequentially designates the second viewpoint movement positions $S_{+20}$ to $S_{n+20}$. In response to the designation of the second viewpoint movement positions $S_{+20}$ to $S_{n+20}$, the display controller 20 obtains the second image addresses $P2_{+20}$ to $P2_{n+20}$ and reads out the second image data stored in the second image storage 42 based on the second image addresses.

The designation of the SEPARATE button 32 described above enables display of the second image corresponding to the second viewpoint movement position on the monitor. In this case, the first image is displayed on the monitor without being changed. The display of the second image on the monitor will be described later.

Thus, the display controller 20 can read out the data of the first image and the second image from the storage 40 based on the observation point movement position (central position), the first viewpoint movement position, and the second viewpoint movement position.

The user interface 10 including the operation part 11, the monitor 12 and the display controller 20 is shown in FIGS. 1 to 3.

When an observation point located on the movement line and corresponding for every predetermined width W is designated by the operation part 11, the display controller 20 reads out the first image obtained by observing across the predetermined width W corresponding to the observation point, from the first image storage 41, and reads out the second image obtained by observing across the predetermined width W corresponding to the observation point, from the second image storage 42. Then, the display controller 20 simultaneously displays the read-out first and second images on the monitor 12.

Figure 5:
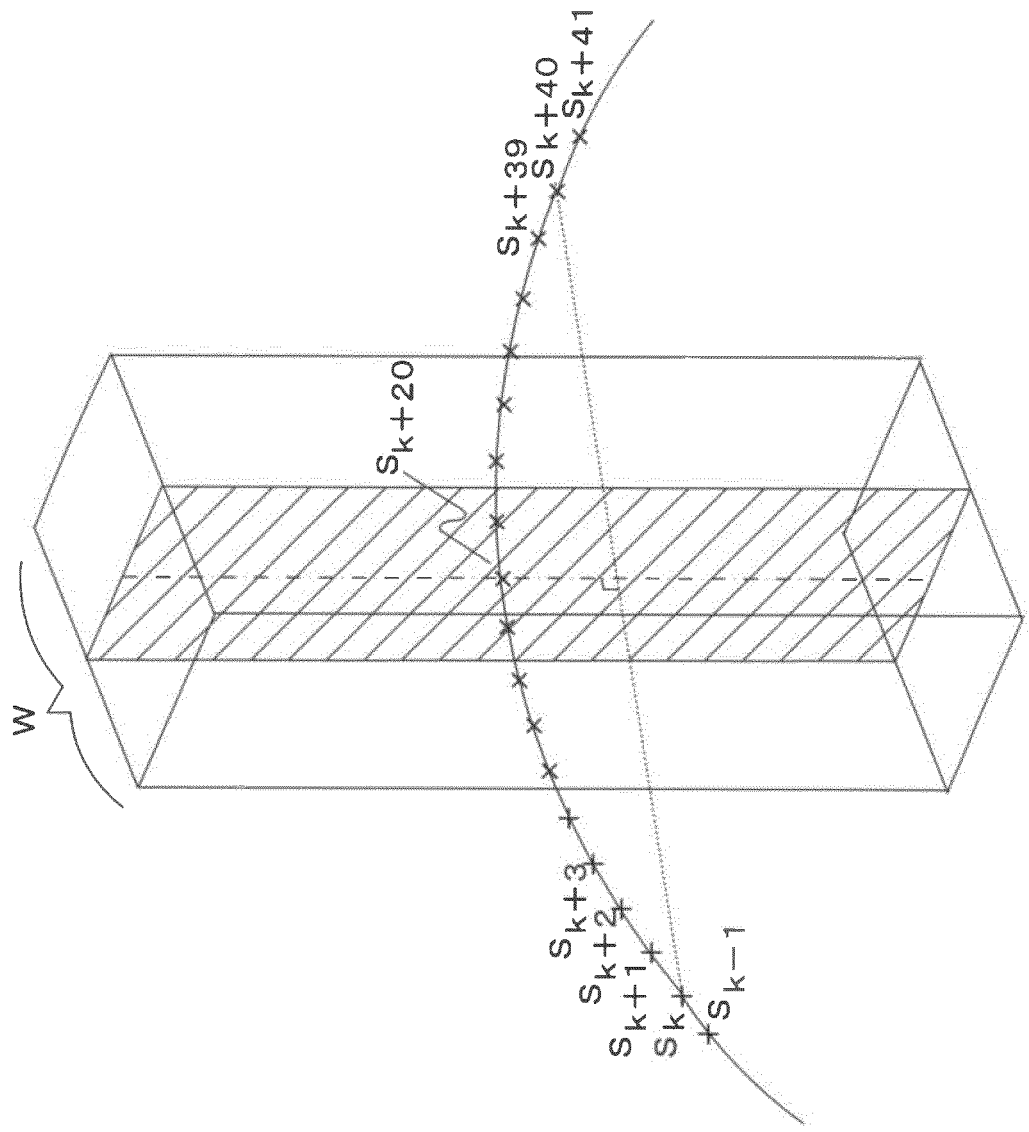
FIG. 5 is a view showing the positional relation of an observation point, a predetermined width and viewpoints according to the embodiment of the present invention.
Figure 6:
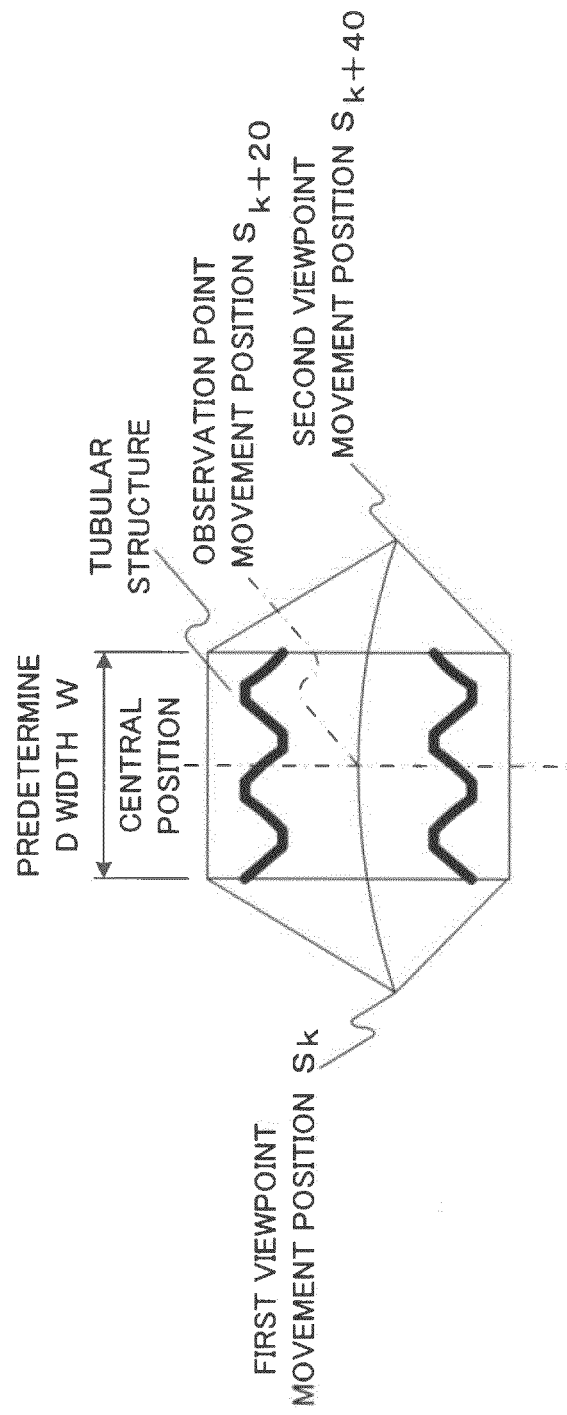
FIG. 6 is a conceptual view illustrating the positional relation of the observation point, the predetermined width and the viewpoints according to the embodiment of the present invention.

Next, the first and second images displayed on the monitor 12 will be described with reference to FIGS. 5 and 6. FIG. 5 is a view showing the positional relation of the observation point, the predetermined width and the viewpoints. FIG. 6 is a conceptual view showing the positional relation of the observation point, the predetermined width and the viewpoints.

The observation point movement position $S_{k+20}$, the first viewpoint movement position $S_k$, the second viewpoint movement position $S_{k+40}$, and the predetermined width W are shown in FIG. 5.

The observation point movement position $S_{k+20}$, the first viewpoint movement position $S_k$, the second viewpoint movement position $S_{k+40}$, the predetermined width W, and the tubular structure included in the predetermined width W as an observation object are shown in FIG. 6 in a conceptual manner.

The first image is an image obtained by observing at the first viewpoint movement position $S_k$ across the predetermined width W corresponding to the observation point movement position $S_{k+20}$. The second image is an image obtained by observing at the second viewpoint movement position $S_{k+40}$ across the predetermined width W corresponding to the observation point movement position $S_{k+20}$. That is to say, the first image and the second image are images obtained by observing across the same predetermined width W from both directions.

The image generator 50 sets the predetermined width W in the following manner. The first viewpoint and the second viewpoint are separated from each other by a predetermined number of points at predetermined pitch $\Delta S$ (1 mm). In this case, the predetermined number is set to an even number of 40, the first viewpoint movement position and the second viewpoint movement position are denoted by $S_k$ and $S_{k+40}$, and the observation point movement position $S_{k+20}$ is set to the central position between the first viewpoint movement position $S_k$ and the second viewpoint movement position $S_{k+40}$.

Thus, the observation point movement positions, the first viewpoint movement positions, the second viewpoint movement positions, and the respective positions of the predetermined widths W are linked. The observation point movement position can be linked to the first viewpoint movement position and the second viewpoint movement position, and is not limited to the central position between the first viewpoint movement position and the second viewpoint movement position. The predetermined number may be an odd number.

Besides, the observation point movement position may be a position that is not between the first viewpoint movement position and the second viewpoint movement position.

Next, such a plane is generated that is orthogonal to a line connecting the first viewpoint movement position $S_k$ and the second viewpoint movement position $S_{k+40}$ and that includes the observation point movement position $S_{k+20}$. The orthogonal plane is hatched and shown in FIG. 5. Two parallel planes, which are parallel to the orthogonal plane and each separated 10 mm from the orthogonal plane on the first viewpoint side and on the second viewpoint side, are generated. The distance between the two parallel planes is the predetermined width W of the default value 20 mm.

When the COORDINATE button 31 and the MOVE button 33 on the operation screen 30 are designated by the operation part 11, the observation point position designating part 111 successively and sequentially designates the observation point movement positions.

When the observation point position designating part 111 designates the observation point movement positions (central positions) $S_0$ to $S_n$, in response to the designation of the observation point movement positions (central positions), a first display controller 21 of the display controller 20 sequentially reads out the first images corresponding to the observation point movement positions from the first image storage 41 and sequentially displays the first images on the monitor 12. Further, a second display controller 22 reads out the second images corresponding to the observation point movement positions from the second image storage 42 and sequentially displays the second images on the monitor 12.

The display controller 20 displays, on the monitor 12, the first image of the predetermined width W observed at the first viewpoint moved from $S_{-20}$ by $\Delta S$ (1 mm) per unit time (e.g., 0.5 second).

Further, the display controller 20 displays, on the monitor 12, the second image of the predetermined width W observed at the second viewpoint moved from $S_{+20}$ by $\Delta S$ (1 mm) per unit time (e.g., 0.5 second).

Accordingly, when the COORDINATE button 31 is designated by the operation part 11, the predetermined width W observed at the first viewpoint and the predetermined width W observed at the second viewpoint are the same predetermined width W.

Although the unit time, which is a time to switch display of the first or second images, is set to 0.5 second, the unit time may be variable. Besides, the observation point position designating part 111 may designate the observation point movement position at every interval of a predetermined number of points (one point or multiple points), instead of successively and sequentially designating the observation point movement position.

Thus, when a STOP button 34 shown in FIG. 1 is designated by the operation part 11 while the display controller 20 is switching and displaying the first or second images at every unit time on the monitor 12, the display controller 20 displays the first or second image obtained when receiving the instruction to stop on the monitor 12.

As described above, when the COORDINATE button 31 and the MOVE button 33 are designated by the operation part 11, the display controller 20 simultaneously displays, on the monitor 12, the first image obtained by observing the predetermined width W of the tubular structure at the first viewpoint (the start point side) and the second image obtained by observing the predetermined width W at the second viewpoint (the end point side). Consequently, blind spots are not created by protrusions existing inside the tubular structure, and a lesion site or the like is easily and certainly found. The designation of the observation point once by the operation part 11 enables display of the first image and the second image. Thus, good operability is achieved.

Next, a case of designating the SEPARATE button 32 and the MOVE button 33 by the operation part 11 will be described.

When the SEPARATE button 32 and the MOVE button 33 on the operation screen 30 are designated by the operation part 11 and, for example, the first viewpoint is designated by the operation part 11, the viewpoint position generator 112 successively and sequentially designates the first viewpoint movement positions. When the viewpoint position generator 112 designates the first viewpoint movement positions $S_{-20}$ to $S_{n-20}$, in response to the designation of the first viewpoint movement positions, the display controller 20 sequentially reads out the first images corresponding to the first viewpoint movement positions from the first image storage 41 and sequentially displays the read-out first images on the monitor 12. The viewpoint position generator 112 may designate the first viewpoint movement position at every interval of a predetermined number of points (one point or multiple points), instead of successively and sequentially designating the first viewpoint movement positions.

The display controller 20 displays, on the monitor 12, the first image of the predetermined width W observed at the first viewpoint moved from $S_{-20}$ by $\Delta S$ (1 mm) per unit time (e.g., 0.5 second).

Meanwhile, the display controller 20 reads out the second image corresponding to the second viewpoint movement position $S_{+20}$, which is the default value, from the second image storage 42, and then displays the second image on the monitor 12.

Accordingly, in a case that the SEPARATE button 32 is designated by the operation part 11, the predetermined width W observed at the first viewpoint and the predetermined width W observed at the second viewpoint are different predetermined widths W.

On the other hand, when the SEPARATE button 32 and the MOVE button 33 on the operation screen 30 are designated by the operation part 11 and, for example, the second viewpoint is designated by the operation part 11, the viewpoint position generator 112 successively and sequentially designates the second viewpoint movement positions. When the viewpoint position generator 112 designates the second viewpoint movement positions $S_{+20}$ to $S_{n+20}$, in response to the designation of the second viewpoint movement positions, the display controller 20 sequentially reads out the second images corresponding to the second viewpoint movement positions from the second image storage 42 and sequentially displays the read-out second images on the monitor 12. The viewpoint position generator 112 may designate the second viewpoint movement position at every interval of a predetermined number of points (one point or multiple points), instead of successively and sequentially designating the second viewpoint movement positions.

The display controller 20 displays, on the monitor 12, the second image of the predetermined width W observed at the second viewpoint moved from $S_{+20}$ by $\Delta S$ (1 mm) per unit time (e.g., 0.5 second). Meanwhile, the display controller 20 reads out, from the first image storage 41, the first image corresponding to the first viewpoint movement position $S_{-20}$, which is the default value, and displays the second image on the monitor 12.

As described above, by a simple operation of merely designating the first viewpoint movement position or the second viewpoint movement position by the operation part, it is possible to selectively observe the inside of the tubular structure from both the directions.

(Operation)

Figure 7:
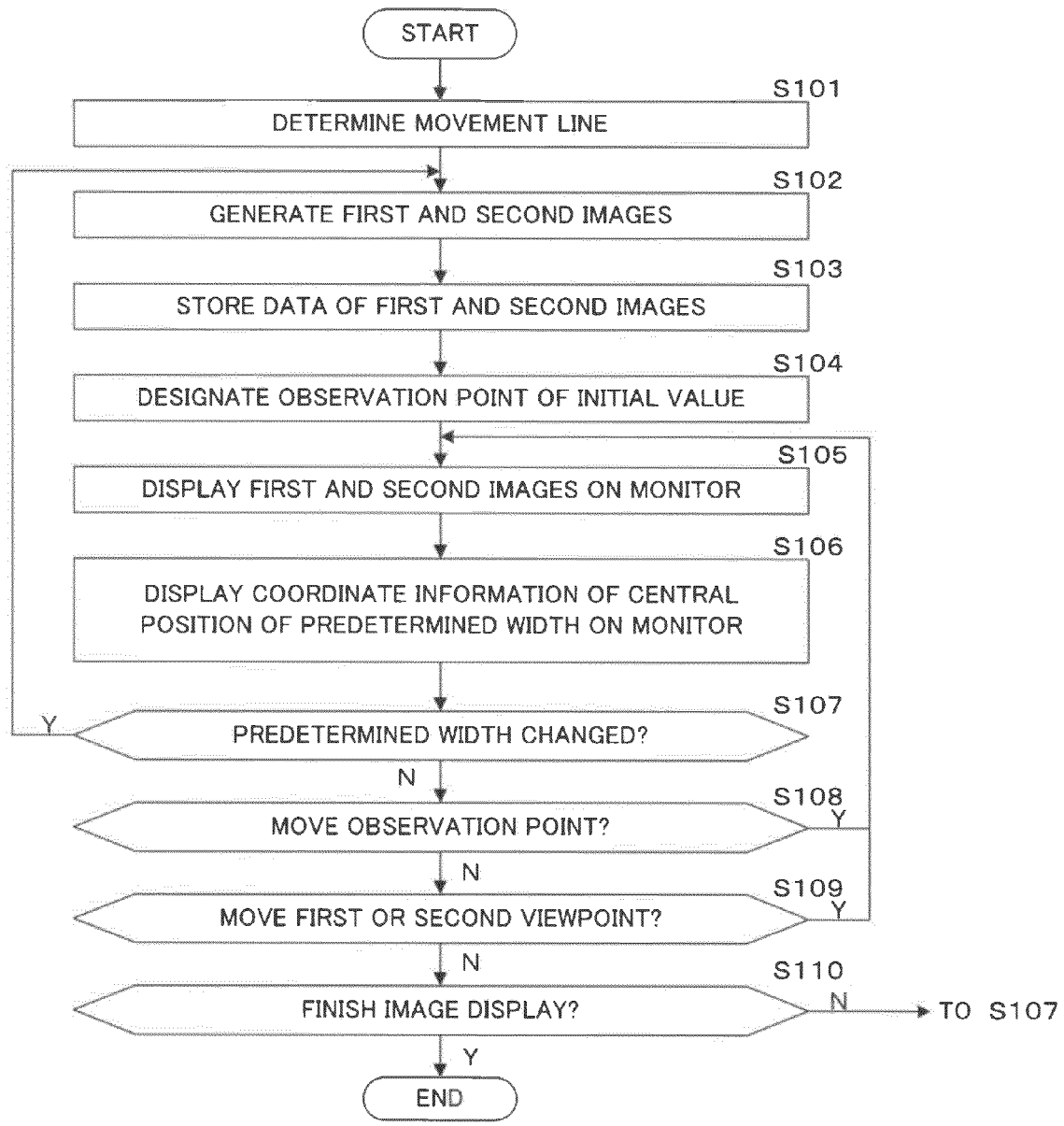
FIG. 7 is a flow chart of a process of specifying the position of a lesion site by using the image display apparatus according to the embodiment of the present invention.

Next, an operation of the image display apparatus when obtaining the coordinate position of a lesion site will be described with reference to FIG. 7. FIG. 7 is a flow chart of a process of specifying the position of a lesion site by using the image display apparatus.

First, an application is executed, and the movement line determining part 54 reads out volume data from the image data storage 43, extracts data representing a tubular structure based on a predetermined threshold from the volume data, and determines a movement line passing through the inside of the tubular structure (step S101). The display controller 20 displays an image of the tubular structure and an image of the movement line on the monitor 12.

Next, the start point position $S_0$ and the end point position $S_n$ on the movement line are designated by the operation part 11. The first image generator 51 generates, by surface rendering, a first image obtained by observing the predetermined width W at a first viewpoint moved from the start point position $S_0$ to the end point position $S_n$ on the movement line. In the same way, the second image generator 52 generates, by surface rendering, a second image obtained by observing the predetermined width W at a second viewpoint moved from the end point position $S_n$ to the start point position $S_0$ on the movement line (step S102).

The first image generator 51 stores data of the generated first image into the first image storage 41. The second image generator 52 stores data of the generated second image into the second image storage 42 (step S103).

The observation point position designating part 111 designates the movement position $S_0$ of the observation point of the default value (step S104). The display controller 20 displays, on the monitor 12, a first image $P1_{-20}$ and a second image $P2_{+20}$ that are linked to the movement position $S_0$ of the observation point of the default value (step S105).

In this case, the display controller 20 displays, on the monitor 12, coordinate information (x1, y1) of the central position of the predetermined width W in the first image and coordinate information (x2, y2) of the central position of the predetermined width W in the second image, as coordinate information ($x_0$, $y_0$) of the movement position $S_0$ of the observation point (step S106). The coordinate position information (x1, y1) of the first viewpoint and the coordinate position information (x2, y2) of the second viewpoint that are displayed on the monitor 12 are shown in FIG. 2.

Next, the user interface 10 determines whether an instruction to change the predetermined width W by the operation part 11 has been received or not (step S107). If the instruction to change the predetermined width W has been received (step S107; Y), the operation returns to step S102 and, in response to information on change of the predetermined width W from the width changing part 53, the image generator 50 generates the first and second images. In a case that the predetermined width W is decreased, the first and second images of the decreased predetermined width W are generated and displayed on the monitor 12. By gradually decreasing the predetermined width W so that a lesion site is included in the first or second image, it is possible to gradually specify the position of the lesion site or the like based on the coordinate information of the central position of the predetermined width W displayed on the monitor 12. Besides, by displaying the lesion site or the like in the central position of the decreased predetermined width W, it is possible to specify the position of the lesion site. Since the coordinate information of the central position of the predetermined width W is displayed on the monitor 12, it is possible to define the coordinate position of the lesion site.

On the other hand, in a case that the predetermined width W is increased, the first and second images of the increased predetermined width W are generated, and the first and second images of the wide predetermined width W are displayed on the monitor 12. Consequently, it is possible to observe the tubular structure across a wide range.

If the instruction to change the predetermined width W has not been received (step S107; N), in response to instructions from the COORDINATE button 31 and the MOVE button 33 by the operation part 11, the user interface 10 determines whether to move the observation point or not (step S108). If the observation point is to be moved (step S108; Y), the operation returns to step S105, and the display controller 20 displays the first image and the second image on the monitor 12. In response to designation of the movement position of the observation point by the observation point position designating part 111, the display controller 20 reads out the first image linked to the movement position of the observation point from the first image storage 41, and also reads out the second image linked to the movement position of the observation point from the second image storage 42.

Then, the display controller 20 displays the read-out first and second images on the monitor 12.

While the observation point is moved in one direction (from the start point side to the end point side on the movement line) or in the other direction (from the end point side to the start point side on the movement line), the first image obtained by observing the predetermined width W of the tubular structure in one direction at the first viewpoint and the second image obtained by observing the predetermined width W of the tubular structure in the other direction at the second viewpoint are displayed on the monitor 12. Accordingly, it is possible to prevent creation of blind spots by protrusions and to certainly find a lesion site.

If the observation point is not to be moved (step S108; N), the user interface 10 determines whether to move the first or second viewpoint or not (step S109). If the first or second viewpoint is to be moved (step S109; Y), the operation returns to step S105, and the first image and the second image are displayed on the monitor 12. In response to information on the movement position of the first viewpoint generated by the viewpoint position generator 112, the display controller 20 reads out the first image from the first image storage 41 and displays the read-out first image on the monitor 12.

Alternatively, the display controller 20 reads out the second image from the second image storage 42 and displays the read-out second image on the monitor 12.

If neither the first viewpoint nor the second viewpoint is to be moved (step S109; N), it is determined whether to end image display (step S110). If image display is not to be ended (step S110; N), the operation returns to step S107, and it is determined whether the predetermined width has been changed or not. If image display is to be ended (step S110; Y), image display is ended.

Although the first image generator 51 writes the first image into the first image storage 41 and the second image generator 52 writes the second image into the second image storage 42 in the above embodiment, the present invention is not limited to this configuration.

For example, the first image generator 51 may write the first image into a buffer of the display controller 20, and the second image generator 52 may write the second image into a buffer of the display controller 20. In this case, the first image storage 41 and the second image storage 42 are the buffers of the display controller 20.

Further, although the observation point is in the central position between the first viewpoint and the second viewpoint (the central position of the predetermined width W) in the above embodiment, the observation point is not limited to the central position. The observation point can be in a position linked to the position of the tubular structure and associated with the first viewpoint and the second viewpoint. In this case, the first image and the second image can be generated corresponding to the first viewpoint, the second viewpoint, and the observation point.

What is claimed is:

1. An image display apparatus that extracts data of a tubular structure from volume data acquired by imaging a subject including the tubular structure, moves a viewpoint so as to pass through the inside of the tubular structure, and displays an image generated by observing an image of the inside of the tubular structure at the viewpoint, the image display apparatus comprising:

a first image generator configured to define one of respective positions between a predetermined start point and end point on a moving line passing through the tubular structure which is located on a side of the start point as a first viewpoint and generate a first image obtained by observing an observation site inside the tubular structure on the side of the end point from the first viewpoint, the first image being generated along the moving line from the start point to the end point;

a second image generator configured to define one of the respective positions between the start point and the end point which is located on an opposite side of the first viewpoint across the observation site as a second viewpoint and generate a second image obtained by observing the observation site on the side of the start point from the second viewpoint, the second image being generated along the moving line from the end point to the start point; and a user interface including an operation part, a monitor, and a display controller, the display controller displaying the first image and the second image at the same time on the monitor in response to an instruction from the operation part, the first image and the second image in a certain region between the first viewpoint and the second viewpoint being viewed from both the first viewpoint and the second viewpoint at the same time.

2. The image display apparatus according to claim 1, wherein the display controller is configured to simultaneously display, on the monitor, the first and second images obtained by observing, from both the viewpoints, a region having a predetermined width between the first and second viewpoints moving while keeping a predetermined distance from each other.

3. The image display apparatus according to claim 1, further comprising a movement line determining part configured to determine a movement line passing through the inside of the tubular structure, wherein:
the first image generator is configured to generate the first image obtained by observing the inside of the tubular structure at the first viewpoint moved along the movement line;
the second image generator is configured to generate the second image obtained by observing the inside of the tubular structure at the second viewpoint moved along the movement line; and
the display controller is configured to, in response to designation of a point on the movement line by the operation part, simultaneously display, on the monitor, the first image corresponding to the designated point and the second image corresponding to the designated point.

4. The image display apparatus according to claim 1, further comprising a movement line determining part configured to determine a movement line passing through the inside of the tubular structure, wherein:
the first image generator is configured to generate the first image obtained by moving the first viewpoint along the movement line;
the second image generator is configured to generate the second image obtained by moving the second viewpoint along the movement line; and
the display controller is configured to display, on the monitor, the first image corresponding to a movement position of the first viewpoint in response to designation of the movement position of the first viewpoint by the operation part, and the second image corresponding to a movement position of the second viewpoint in response to designation of the movement position of the second viewpoint by the operation part.

5. The image display apparatus according to claim 2, further comprising a width changing part configured to change the predetermined width in response to designation by the operation part.

6. The image display apparatus according to claim 2, wherein the display controller is configured to display each coordinate of the central position of the predetermined width on the monitor.

7. The image display apparatus according to claim 5, wherein the display controller is configured to display each coordinate of the central position of the predetermined width on the monitor.

8. An image display method, comprising:
extracting data representing a tubular structure based on a predetermined threshold from volume data acquired by imaging a subject including the tubular structure, and determining a movement line passing through the inside of the tubular structure;
while moving a first viewpoint from a predetermined start point to a predetermined end point along the movement line, generating a first image of the inside of the tubular structure of at a movement destination of the first viewpoint from the first viewpoint for every movement position of the first viewpoint;
while moving a second viewpoint from the predetermined end point to the predetermined start point along the movement line, generating a second image of the inside of the tubular structure of a movement destination of the second viewpoint from the second viewpoint for every movement position of the second viewpoint;
when a point on the movement line is designated by the operation part, by a display controller, simultaneously displaying the first image corresponding to the point designated by the operation part and the second image corresponding to the point designated by the operation part, on the monitor;
in response to an instruction by the operation part to change a predetermined width of the inside of the tubular structure displayed on the monitor, changing the predetermined width and generating the first image based on the changed predetermined width;
in response to an instruction by the operation part to change the predetermined width, changing the predetermined width and generating the second image based on the changed predetermined width;
by a display controller, displaying the first image corresponding to the movement position of the first viewpoint in response to designation of the movement position of the first viewpoint by the operation part, and displaying the second image corresponding to the movement position of the second viewpoint in response to designation of the movement position of the second viewpoint by the operation part, on the monitor; and
by the display controller, displaying coordinates of positions on the movement line on the monitor, the coordinates being coordinates of a central position of the predetermined width of the movement destination of the first viewpoint and coordinates of the central position of the predetermined width of the movement destination of the second viewpoint.

9. The image display method according to claim 8, comprising:
generating a first image of the inside of the tubular structure of an observation site at a movement destination of the first viewpoint; and
generating a second image of the inside of the tubular structure of the observation site at a movement destination of the second viewpoint;
the second viewpoint being located on an opposite side of the observation site as the first viewpoint.

* * * * *